(12) United States Patent
Racenet et al.

(10) Patent No.: US 10,595,871 B2
(45) Date of Patent: Mar. 24, 2020

(54) INSERTION INSTRUMENT, ADAPTER ASSEMBLIES AND PROTECTOR ASSEMBLIES FOR A FLEXIBLE CIRCULAR STAPLER

(71) Applicant: Covidien LP, Mansfield, MA (US)

(72) Inventors: David Racenet, Killingworth, CT (US); Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 288 days.

(21) Appl. No.: 15/583,594

(22) Filed: May 1, 2017

(65) Prior Publication Data
US 2017/0325817 A1 Nov. 16, 2017

Related U.S. Application Data

(60) Provisional application No. 62/334,145, filed on May 10, 2016.

(51) Int. Cl.
*A61B 17/115* (2006.01)
*A61B 17/072* (2006.01)
(Continued)

(52) U.S. Cl.
CPC .... *A61B 17/1155* (2013.01); *A61B 17/07207* (2013.01); *A61B 34/30* (2016.02); *A61B 90/30* (2016.02); *A61B 90/361* (2016.02); *A61B 2017/0046* (2013.01); *A61B 2017/00323* (2013.01); *A61B 2017/00336* (2013.01); *A61B 2017/00473* (2013.01); *A61B 2017/00477* (2013.01); *A61B 2017/00557* (2013.01); *A61B 2017/00734* (2013.01);
(Continued)

(58) Field of Classification Search
CPC ..... A61B 34/30; A61B 17/3462; A61B 34/74; A61B 34/37; A61B 34/35; B25J 13/088
USPC ....................................................... 227/179.1
See application file for complete search history.

(56) References Cited

U.S. PATENT DOCUMENTS

| 3,193,165 A | 7/1965 | Akhalaya et al. |
|---|---|---|
| 3,388,847 A | 6/1968 | Kasulin et al. |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Dec. 11, 2017, issued in EP Application No. 17170075.

(Continued)

*Primary Examiner* — Nathaniel C Chukwurah
(74) *Attorney, Agent, or Firm* — Carter, DeLuca & Farrell LLP

(57) ABSTRACT

An adapter assembly for connecting a handle assembly with a loading unit is provided. The adapter assembly includes a housing, an elongate body extending from the housing, and a trocar assembly supported within the elongate body and including a trocar member. The trocar member extends from the elongate body and is magnetized. Also provided are various assemblies for protecting the distal end of a surgical stapler during introduction of the surgical stapler within a patient.

15 Claims, 13 Drawing Sheets

(51) Int. Cl.
- *A61B 17/00* (2006.01)
- *A61B 90/00* (2016.01)
- *A61B 90/30* (2016.01)
- *A61B 34/30* (2016.01)

(52) U.S. Cl.
CPC ........... *A61B 2017/00876* (2013.01); *A61B 2017/07285* (2013.01); *A61B 2090/08021* (2016.02); *A61B 2090/309* (2016.02); *A61B 2217/007* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A * | 7/1994 | Wilk ............... A61B 17/068 227/179.1 |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A * | 9/1994 | Main ............... A61B 17/115 227/179.1 |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |

(56) References Cited

U.S. PATENT DOCUMENTS

| | | | |
|---|---|---|---|
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |

(56) References Cited

U.S. PATENT DOCUMENTS

| | | |
|---|---|---|
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0075117 A1* | 4/2007 | Milliman ............ A61B 17/115 227/179.1 |
| 2008/0300609 A1 | 12/2008 | Tabet |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0170281 A1 | 7/2011 | Shih |
| 2011/0192882 A1 | 8/2011 | Hess et al. |
| 2012/0145755 A1 | 6/2012 | Kahn |
| 2012/0193395 A1 | 8/2012 | Pastorelli et al. |

(56) References Cited

U.S. PATENT DOCUMENTS

| | | |
|---|---|---|
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1* | 7/2013 | Felder .............. A61B 17/1155 227/175.2 |
| 2013/0175319 A1 | 7/2013 | Felder et al. |
| 2013/0175320 A1* | 7/2013 | Mandakolathur Vasudevan ......... A61B 17/072 227/175.2 |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0141976 A1* | 5/2015 | Stulen .................... A61B 18/04 606/28 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2799026 A2 | 11/2014 |
| EP | 2954857 A1 | 12/2015 |
| EP | 2992841 A2 | 3/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2006014881 A2 | 2/2006 |
| WO | 2008/107918 A1 | 9/2008 |
| WO | 2011149876 A2 | 12/2011 |
| WO | 2015073425 A1 | 5/2015 |

OTHER PUBLICATIONS

European Search Report dated Sep. 6, 2017, issued in EP Application No. 17170075.

* cited by examiner

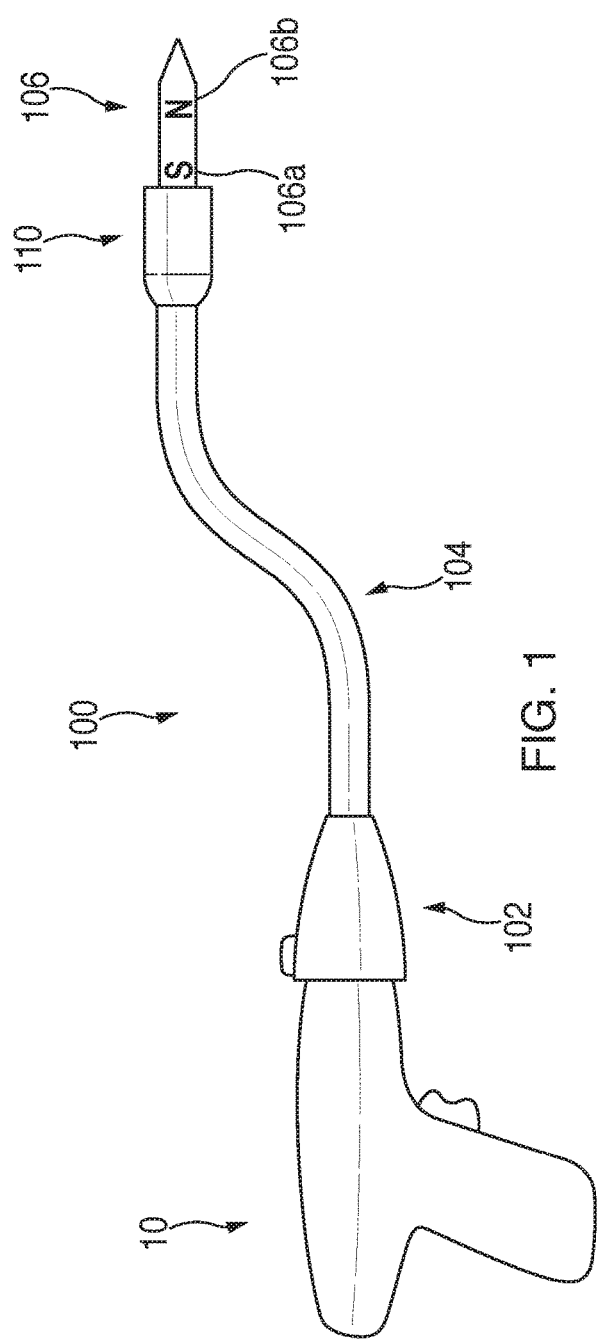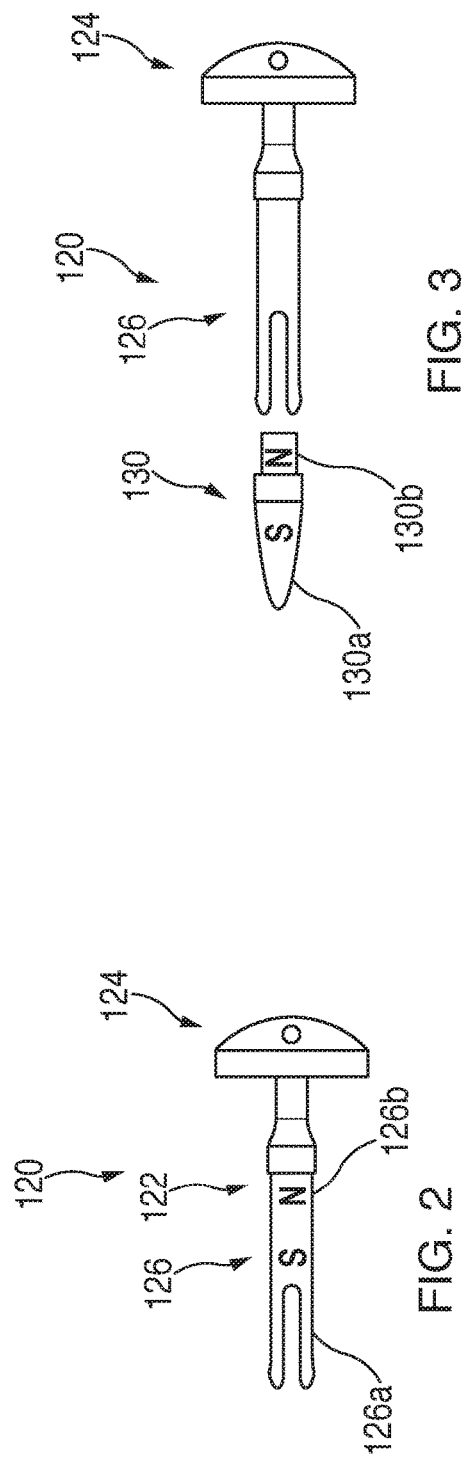

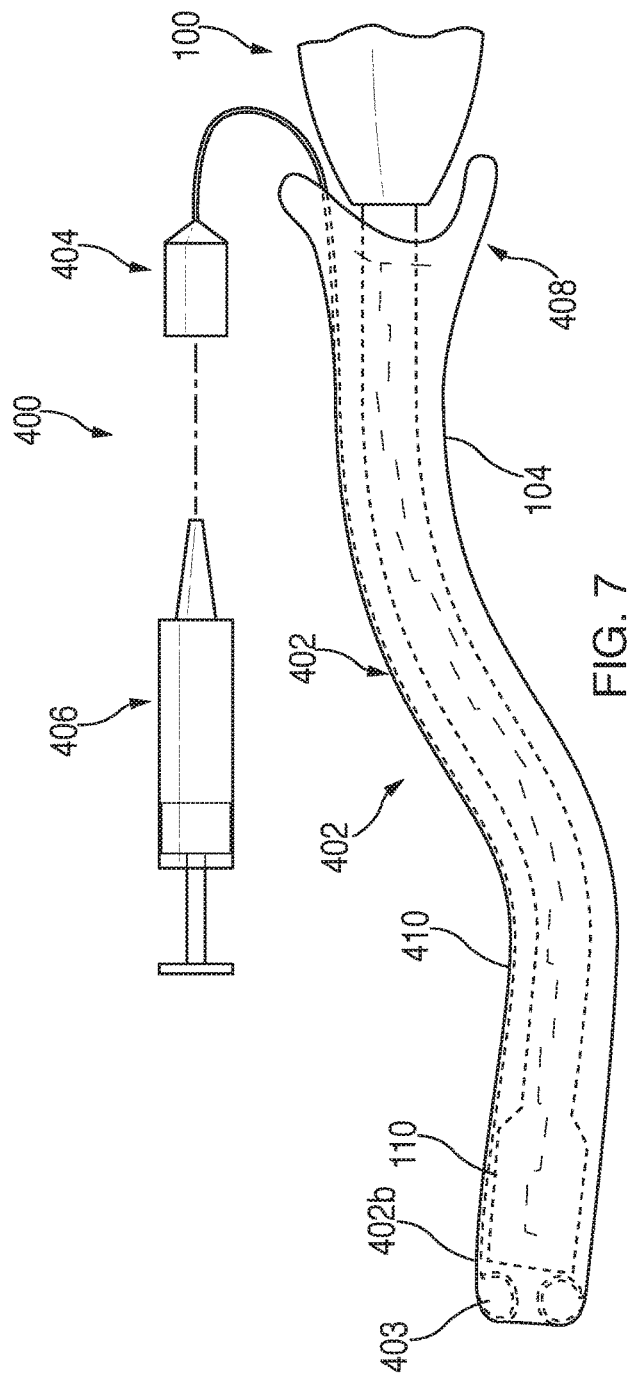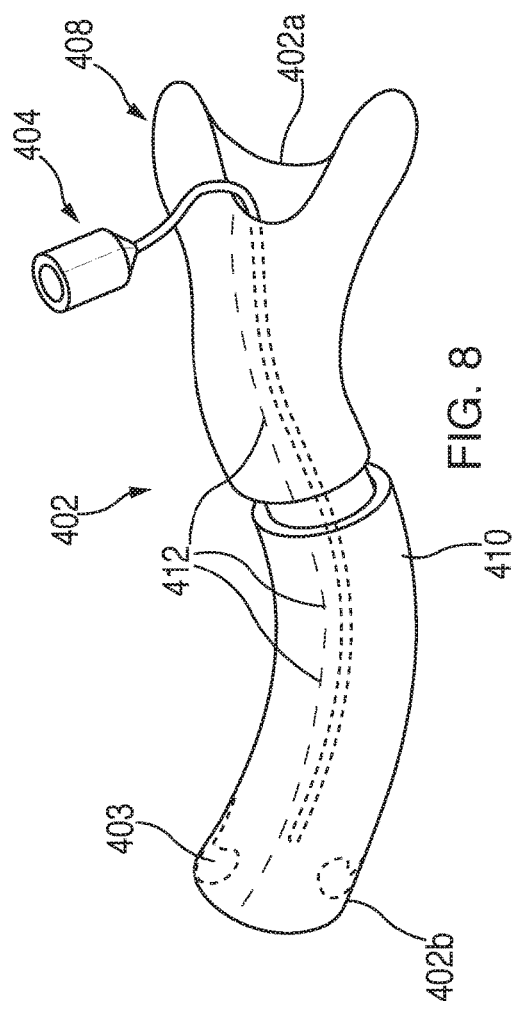

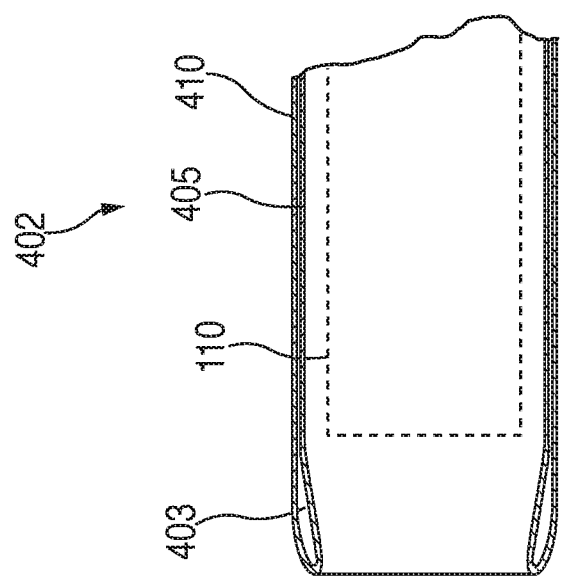
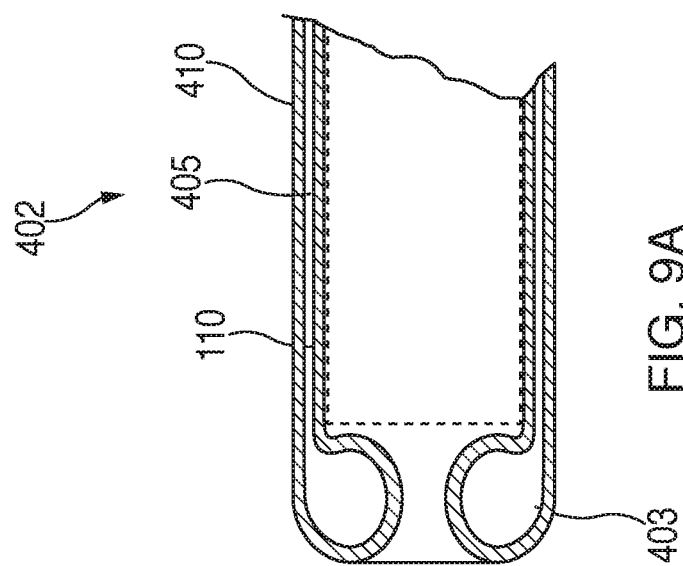

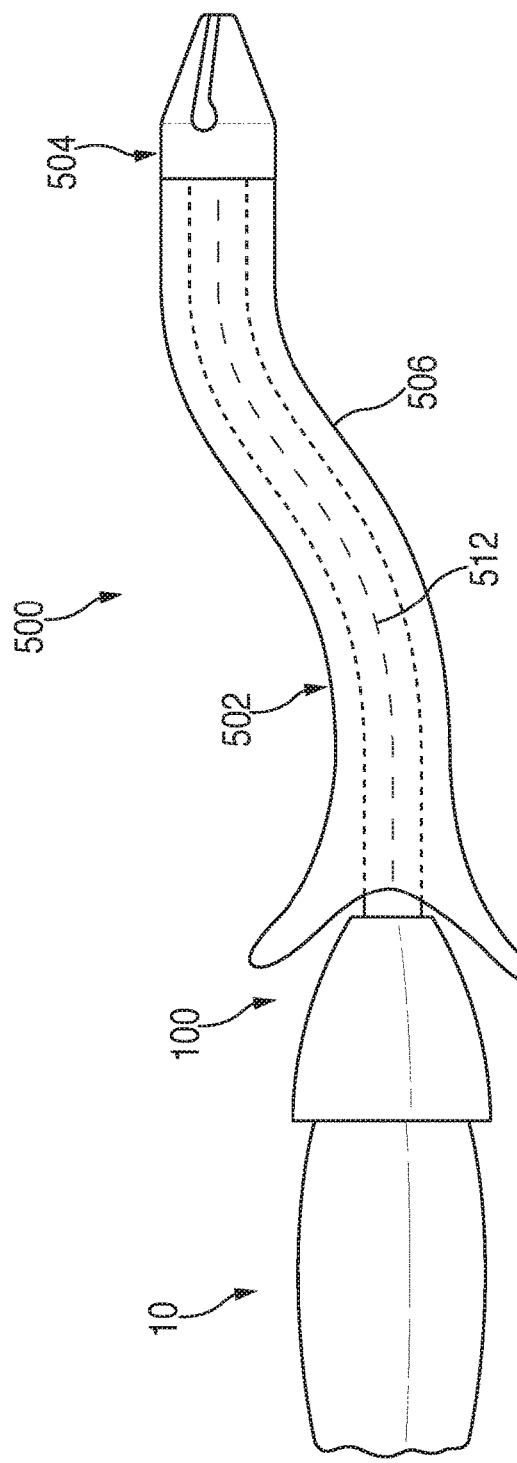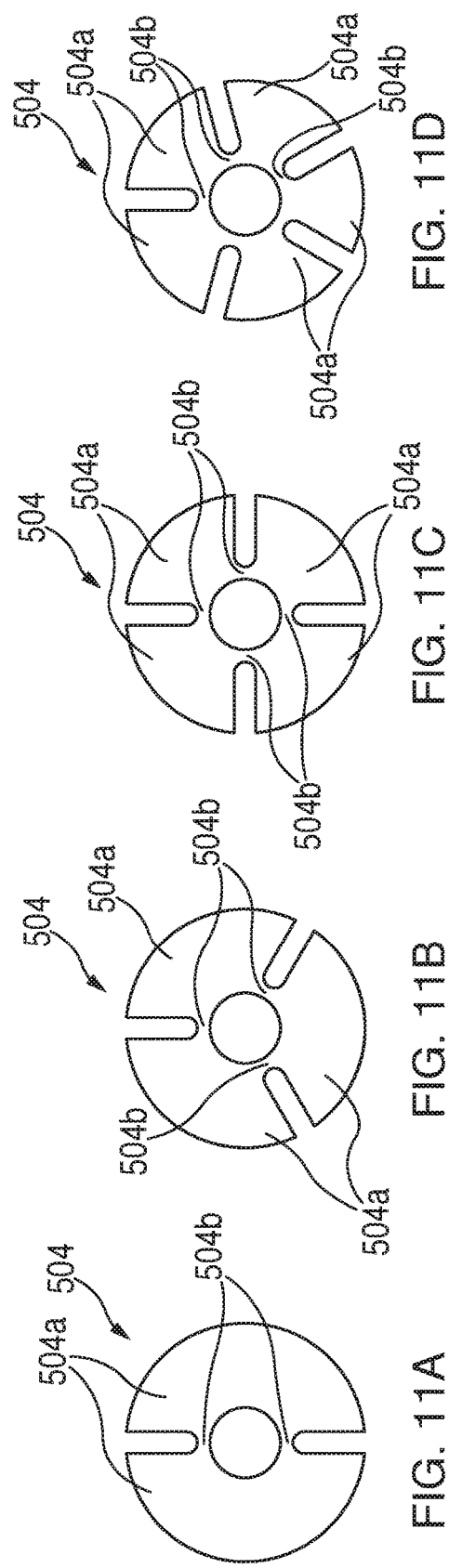

INSERTION INSTRUMENT, ADAPTER ASSEMBLIES AND PROTECTOR ASSEMBLIES FOR A FLEXIBLE CIRCULAR STAPLER

CROSS-REFERENCE TO RELATED APPLICATIONS

This application claims the benefit of and priority to U.S. Provisional Patent Application Ser. No. 62/334,145, filed May 10, 2016, the entire disclosure of which is incorporated by reference herein.

BACKGROUND

Technical Field

The present disclosure relates to surgical stapling devices. More particularly, the present disclosure relates to insertion instruments, adapter assemblies, and protector assemblies for powered flexible circular staplers.

Background of Related Art

Circular staplers are used to perform end to end anastomosis. During a typical surgical procedure, an anvil of the circular stapler is delivered to the surgical site while a staple cartridge of the circular stapler supported on an elongate shaft is inserted through an incision in, for example, the abdominal wall. Alternatively, the circular stapler may include a flexible shaft that permits introduction of the staple cartridge to the surgical site through a natural body orifice, e.g., mouth or anus. The circular staplers may be manual or powered, and may be modified for use with robotic surgical systems.

In order to better facilitate introduction and positioning of a flexible shaft of the circular staplers, it would be beneficial to have a circular stapler that includes an efficient mechanism for connecting the anvil assembly of the circular stapler to the elongate body of the circular stapler during a surgical procedure. It would also be beneficial to have an introducer that minimizes risk of damage to the patient and/or to the circular stapler during, for example, introduction of the circular stapler into a patient. It would further be beneficial to have a circular stapler that increases visualization of the surgical procedure. It would also be beneficial to have a circular stapler with an elongated body capable of accommodate a guide wire and/or that allows for injecting saline to an anastomosis site to, for example, test a seal and ease manipulation.

SUMMARY

An adapter assembly for connecting a handle assembly with a loading unit is provided. The adapter assembly includes a housing, an elongate body extending from the housing, and a trocar assembly supported within the elongate body and including a trocar member. The trocar member extends from the elongate body. wherein the trocar member is magnetized.

In embodiments, the adapter assembly includes an anvil assembly. The anvil assembly may include a center rod magnetized to compliment the trocar member such that the center rod is magnetically attracted to the trocar member. The anvil assembly may include a removable tip. The removable tip may be magnetized to compliment the trocar member such that the removable tip is magnetically attracted to the trocar member. The trocar assembly may include an electromagnet received about the trocar member for selectively magnetizing the trocar member. The adapter assembly may further include a light source.

Also provided is an insertion instrument for facilitating placement of an anvil assembly within a patient. The insertion instrument includes a handle assembly, an elongate body extending from the handle assembly, an electromagnet including a coil of wire received around a ferromagnetic member, the electromagnet being disposed on a distal end of the elongate body, and a light source disposed on a distal end of the elongate body. In embodiments, the insertion instrument includes a first switch assembly for selectively activating the electromagnet. The insertion instrument may include a second switch assembly for selectively activating the light source.

Another assembly for protecting the functional end of a surgical stapler during introduction of the surgical stapler within a patient is provided. The assembly includes a sleeve having proximal and distal ends and being receivable about an elongate body. The sleeve defines an inflatable cavity on the distal end configured to be disposed adjacent a distal end of the elongate body. The assembly also includes an insufflation port in fluid communication with the inflatable cavity for selectively inflating the inflatable cavity.

In embodiments, the sleeve further defines a weakened portion extending along the length of the sleeve. The sleeve may include a handle portion on the proximal end. The assembly may include a source of insufflation fluid. The source of insufflation fluid may include a syringe.

An assembly for protecting the functional end of a surgical stapler is also provided. The assembly includes a sleeve having proximal and distal ends, and a cap member secured to the distal end of the sleeve. The cap member may include a plurality of leaves connected to each other by a frangible connection. The frangible connection may include a weakened bridge.

In embodiments, the sleeve includes a handle portion on the proximal end. The sleeve may further define a weakened portion extending along the length of the sleeve. The assembly may also include a camera disposed on a distal end of the cap member. The assembly may include a steering assembly having a steering ring and a plurality of steering cables secured to the steering ring. The plurality of steering cables may extend the length of the sleeve.

Also provided is an assembly for protecting a distal end of circular stapling apparatus. The assembly includes an inflatable member having a first portion and a second portion, wherein the first portion is smaller than the second portion and is configured to be received within the distal end of a loading unit. The assembly also includes an insufflation port operably connected to the inflatable member for selectively inflating and deflating the inflatable member.

In embodiments, the inflatable member includes a snowman shape. Each of the first and second portions may be substantially spherical.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a side view of an exemplary handle assembly and an adapter assembly according to an embodiment of the present disclosure;

FIG. 2 is a side view of an anvil assembly according to an embodiment of the present disclosure;

FIG. 3 is a side view of an anvil assembly according to another embodiment of the present disclosure;

FIG. 7 is a perspective side view of a protective assembly according to an embodiment of the present disclosure received about the adapter assembly shown in FIG. 1;

FIG. 8 is a perspective side view of a sleeve member of the protective assembly shown in FIG. 7;

FIG. 9A is an enlarged side view of the distal end of the sleeve member shown in FIG. 8, in a first or inflated condition;

FIG. 9B is an enlarged side view of the distal end of the sleeve member shown in FIG. 8, in a second or deflated condition;

FIG. 10 is a perspective side view of a protective assembly according to another embodiment of the present disclosure received about the adapter assembly shown in FIG. 1;

FIGS. 11A-11D are end views of cap members of the protective assembly shown in FIG. 10, having two (FIG. 11A), three (FIG. 11B), four (FIG. 11C), and five (FIG. 11D) leaves;

DETAILED DESCRIPTION

Figure 4:
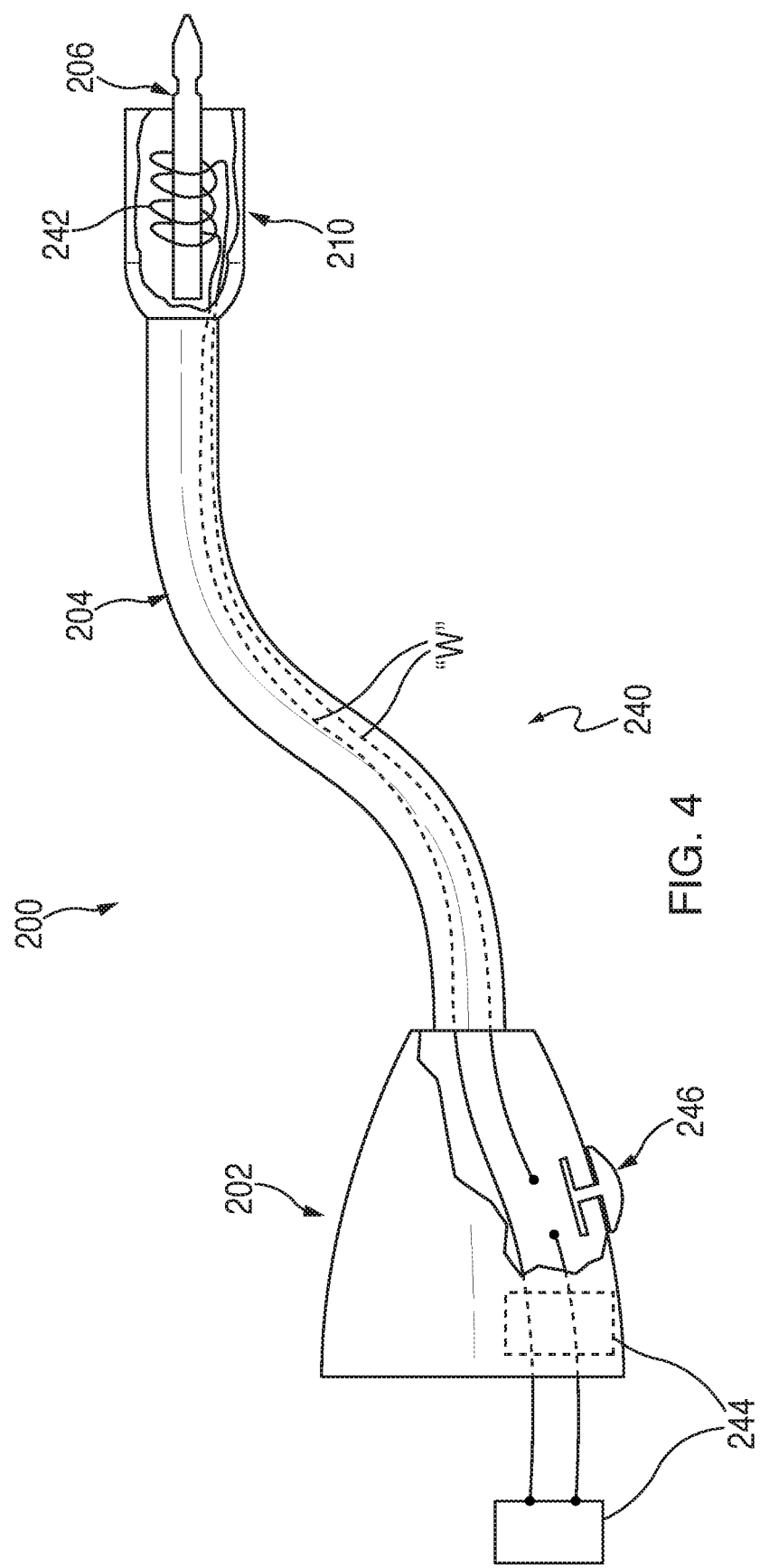
FIG. 4 is a side view of an adapter assembly according to another embodiment of the present disclosure.

Embodiments of the disclosure are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

The embodiments of the present disclosure will be described in detail with respect to a powered handle assembly 10. Although shown and described as relates to the powered handle assembly 10, it is envisioned that the embodiments of the present disclosure may be modified for use with powered and non-powered handle assemblies having various configurations. For a detailed description of an exemplary powered circular stapler, please refer to commonly owned U.S. Pat. Appl. Publ. No. 2012/0253329 ("the '329 application"), the content of which is incorporated by reference herein in its entirety. Also, for a detailed description of an exemplary electromechanical powered handle assembly, please refer to commonly owned U.S. Pat. Appl. Publ. No. 2015/0157320 ("the '320 application), the content of which is incorporated by reference herein in its entirety.

With continued reference to FIG. 1, an adapter assembly according to an embodiment of the present disclosure is shown generally as adapter assembly 100. The adapter assembly 100 will only be described to the extent necessary to fully disclose the aspects of the present disclosure. For a detailed description of exemplary adapter assemblies, please refer to commonly owned U.S. Prov. Pat. Appl. Ser. No. 62/239,301, filed Oct. 9, 2015 and U.S. Prov. Pat. Appl. Ser. No. 62/251,300, filed Nov. 5, 2015, the contents of each of which are incorporated by reference herein in their entirety.

The adapter assembly 100 releasably connects to the powered handle assembly 10. The adapter assembly 100 includes a housing 102 operably connectable to the powered handle assembly 10, and an elongate body 104 extending from the housing 102. A loading unit 110 may be integrated with the adapter assembly 100, or may be releasably coupled to the adapter assembly 100 to permit reuse of the adapter assembly 100. The elongate body 104 is flexible to facilitate insertion of the loading unit 110 within the body.

A trocar member 106 extends from a distal end of the elongate body 104 for releasably engaging an anvil assembly, i.e., anvil assembly 120 (FIG. 2). As shown, a proximal portion 106a of the trocar member 106 includes a first magnetic polarity, i.e., south "S", and a distal portion 106b of the trocar member 106 includes a second magnetic polarity, i.e., north "N". As will become apparent from the below description, the polarities of the proximal and distal portions 106a, 106b of the trocar member 106 may be switched.

With reference to FIG. 2, the anvil assembly 120 is configured for releasable connection to the trocar member 106 (FIG. 1) of the adapter assembly 100 (FIG. 1). The anvil assembly 120 will only be described to the extent necessary to fully disclose the aspects of the present disclosure. For a detailed description of an exemplary anvil assembly, please refer to commonly owned U.S. Pat. No. 7,364,060 ("the '060 patent"). Another example of a tiltable anvil assembly is disclosed in commonly owned U.S. Pat. No. 8,540,132 ("the '132 patent"). The content of each of the '060 patent and the '132 patent are incorporated herein by reference in their entirety.

Briefly, the anvil assembly 120 includes a center rod assembly 122, and an anvil head assembly 124 secured to the center rod assembly 122. The head assembly 124 of the anvil assembly 120 may be rigidly secured to the center rod assembly 122. Alternatively, the head assembly 124 may be pivotally secured to the center rod assembly 122 to facilitate insertion of the anvil assembly 120 through a lumen of a patient. The center rod assembly 122 of the anvil assembly 120 includes a center rod 126. In one embodiment, the center rod 126 is magnetized. As shown in FIG. 2, the center rod 126 includes a proximal portion 126a with a first magnetic polarity, i.e., south "S", and a distal portion 126b with a second magnetic polarity, i.e., north "N".

As noted above, the trocar member 106 (FIG. 1) of the adapter assembly 100 (FIG. 1) is magnetized in a similar manner to the center rod 126 of the anvil assembly 120. In this manner, the proximal portion 126a of the center rod 126 of the anvil assembly 120 is attracted to the distal portion 106b of the trocar member 106.

During a surgical stapling procedure, the anvil assembly 120 may be introduced to a surgical site trans-orally, or in any other manner. After securing a first section of tissue to be stapled (not shown) to the anvil assembly 120, and after securing a second section of tissue to be stapled (not shown) about the loading unit 110 of the adapter assembly 100, the adapter assembly 100 is moved towards the anvil assembly 120. The magnetic attraction between the proximal portion 126a of the center rod 126 of the anvil assembly 120 and the distal portion 106b of the trocar member 106 facilitates alignment of the center rod 126 of the anvil assembly 120 with the trocar member 106 of the adapter assembly 100. This feature is particularly beneficial when the anvil assembly 120 is not visible to the clinician during connection of the anvil assembly 120 to the adapter assembly 100.

Turning to FIG. 3, in an alternative embodiment, the anvil assembly 120 includes a removable tip member 130 for facilitating receipt of the center rod 126 of the anvil assembly 120 through tissue (not shown). The removable tip member 130 includes a proximal portion 130a configured for piercing tissue and a distal end 130b configured for operable connection to the proximal end 126a of the center rod 126. The proximal portion 130a of the removable tip member 130 includes a first magnetic polarity, i.e., south "S", and the distal portion 130b of the removable tip member 130 includes a second magnetic polarity, i.e., north "N". When the removable tip member 130 is secured to the center rod 126 of the anvil assembly 120, in a manner similar to the magnetized center rod 126 described above, the magnetic attraction between the proximal portion 130a of the removable tip member 130 and the distal portion 106b (FIG. 1) of the trocar member 106 (FIG. 1) of the adapter assembly 100 (FIG. 1) facilitates approximation of the anvil assembly 120 to the adapter assembly 100.

Turning now to FIG. 4, an alternative embodiment of an adapter assembly according to the present disclosure is shown generally as adapter assembly 200. The adapter assembly 200 is substantially similar to adapter assembly 100 described hereinabove. The adapter assembly 200 includes a housing 202, an elongate body 204 extending from the housing 202, a trocar member 204 extending from the elongate body 204 for releasably securing an anvil assembly, e.g., anvil assembly 120 (FIG. 2), and a loading unit 210 disposed on a distal end of the elongate body 204.

With continued reference to FIG. 4, the adapter assembly 200 includes an electromagnet assembly 240. The electromagnet assembly 240 includes a wire coil or solenoid, 242 disposed within the loading unit 210 of the adapter assembly 200 and about the trocar member 206. The wire coil 242 is connected to a power source 244. The power source 244 may be disposed within the housing 202 of the adapter assembly 200, within the handle assembly 10 (FIG. 1), as a standalone power source, or in any other suitable configuration. A switch 246 for activating the electromagnet assembly 240 may be disposed on the housing 202 of the adapter assembly 200, as shown, or may be disposed on the handle assembly 10 (FIG. 1), or as an independent actuator i.e., foot pedal (not shown).

Activation of the electromagnet assembly 240 of the adapter assembly 200 magnetizes the trocar member 206. As described above with regards to the trocar member 106 of the adapter assembly 100, when the trocar member 206 of the adapter assembly 200 is magnetized, an anvil assembly that includes a magnetized portion, i.e., the center rod 126, the removable trocar tip 130, is attracted to the trocar member 206 to facilitate connection of the anvil assembly to the trocar member 206.

Figure 5:
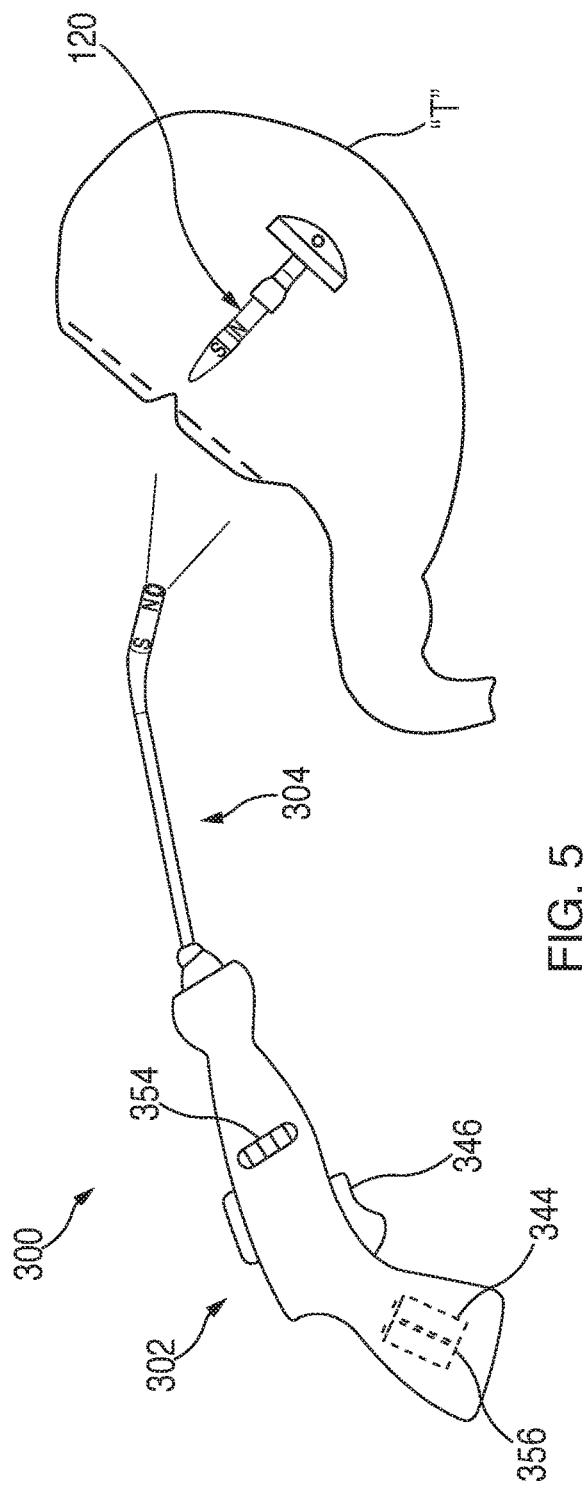
FIG. 5 is a perspective view of an insertion instrument and anvil assembly according to an embodiment of the present disclosure.
Figure 6:
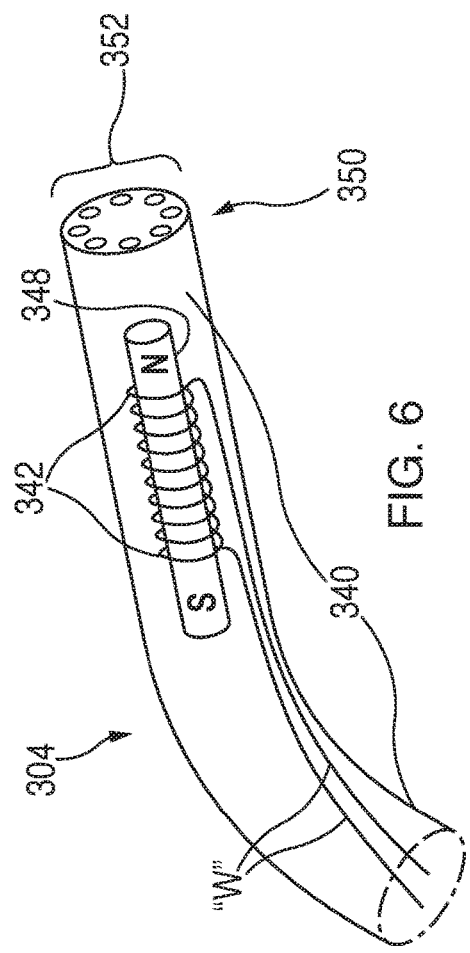
FIG. 6 is an enlarged perspective side view of the distal end of the insertion instrument shown in FIG. 5.

With reference now to FIGS. 5 and 6, an instrument for facilitating positioning of a magnetized anvil assembly, i.e., the anvil assembly 120, within a patient is shown generally as insertion instrument 300. The insertion instrument 300 includes a handle assembly 302, and an elongate body 304 extending from the handle assembly 302. The insertion instrument 300 also includes an electromagnet assembly 340 and a light assembly 350.

The electromagnet assembly 340 is similar to the electromagnet assembly 240 of the adapter assembly 200, and includes a wire coil 342 wrapped about a ferromagnetic material, i.e., rod member 348, a power source 344 connected to the wire coil 342, and an activation switch 346 for activating the electromagnet assembly 340.

The light assembly 350 includes at least one light source, for example, a circular array of light emitting diodes 352 mounted on a distal end of the elongate body 304, and a control switch for activating the light source 352 and for controlling the intensity of the light source 352. The light source 352 may be powered by the power source 344 of the electromagnet assembly 340. Alternatively, the light source 352 may be powered by an independent power source disposed within the handle assembly 302.

During positioning of the anvil assembly 120, activation of the electromagnet assembly 340 of the insertion instrument 300 creates a magnetic field that attracts the magnetized center rod 126 (FIG. 2) of the anvil assembly 120 to facilitate positioning of the anvil assembly 120 within the body cavity and through tissue "T". Activation of the light source 352 of the light assembly 352 facilitates viewing of the anvil assembly 120 as the anvil assembly 120 is positioned through the tissue "T". It is envisioned that the light source 352 may be placed behind the tissue "T" to illuminate the tissue "T".

With reference now to FIG. 7, an assembly for protecting the elongate body 104 of the adapter assembly 100 and the loading unit 110 that is secured to the elongate body 104, and for minimizing damage to tissue of a patient during introduction of the adapter assembly 100 within the patient, is shown generally as protective assembly 400. The protective assembly 400 includes a sleeve member 402, and an insufflation port 404 operably connected to the sleeve member 402. The insufflation port 404 may include a luer connector or other suitable connection. The protective assembly 400 further includes a syringe 406 or other source of insufflation fluid, i.e., air canister, bellow pump, configured for operable connection with the insufflation port 404.

With additional reference to FIG. 8, the sleeve member 402 of the protective assembly 400 includes an elongate flexible body 410 configured to be received about the elongate body 104 (FIG. 7) of the adapter assembly 100 (FIG. 7) and the loading unit 110 (FIG. 7) that is secured to the elongate body 102 of the adapter assembly. The sleeve member 402 includes open proximal and distal ends 402a, 402b, and defines an inflatable annular cavity or donut 403 extending about the open distal end 402b in fluid communication with the insufflation port 404. As will be described in further detail below, the inflatable donut 403 is configured to be positioned adjacent the distal end of the elongate body 104 for protecting the adapter assembly 100 from damage during introduction of the adapter assembly 100 into a patient, and for protecting the tissue of the patient. The inflatable donut 403 is connected to the insufflation port 404 by one or more inflation channels 405 extending along the length of the elongate flexible body 410 of the sleeve member 402.

The open proximal end 402a of the sleeve member 402 includes a handle member or pull back handle 408 for facilitating receipt of the sleeve member 402 about the elongate body 104 of the adapter assembly 100, and for facilitating removal of the sleeve member 402 from about the elongate body 104. The sleeve member 402 may include a perforation or tear-line 412 extending along all or a portion of the length of the elongate flexible body 410. Alternatively, the sleeve member 402 may by formed of a sheet of material having a hook and loop type fastener (e.g., Velcro®), or zip lock connection, for maintaining the tubular structure.

During a surgical procedure, and prior to introduction of the elongate body 104 of the adapter assembly 100 into a patient, the sleeve member 402 of the protective assembly 400 is received about the elongate body 104. The sleeve member 402 of the protective assembly 400 may be received about the elongate body 102 when the sleeve member 402 is in an inflated configuration (FIG. 9A), or when sleeve member 402 is in a deflated configuration (FIG. 9B). The sleeve member 402 is retracted about the elongate body 402 until the inflatable annular cavity 403 is disposed adjacent the distal end of the elongate body 104. If the inflatable annular cavity 403 of the sleeve member 402 is not already inflated, the syringe 406 (FIG. 7) may be used to inflate the inflatable annular cavity 403.

During introduction of the elongate body 104 of the adapter assembly 100 into a patient, the sleeve member 402 of the protective assembly 400 protects the distal end of the elongate body 104 from damage, while also protecting the tissue through which the adapter assembly 100 is introduced. Once the adapter assembly 100 has been positioned within the patient, the inflatable annular cavity 403 of the sleeve member 402 of the protective assembly 400 may be deflated to facilitate removal of the sleeve member 402 from the elongate body 104 of the adapter assembly 100. As noted above, the sleeve member 402 may include perforation or tear-line 412 for facilitating removal of the sleeve member 402 from about the elongate body 104. Once the sleeve member 402 of the protective assembly 400 is removed from about the elongate body 104 of the adapter assembly 100, the adapter assembly 100 may be used in a traditional manner.

Figure 12:
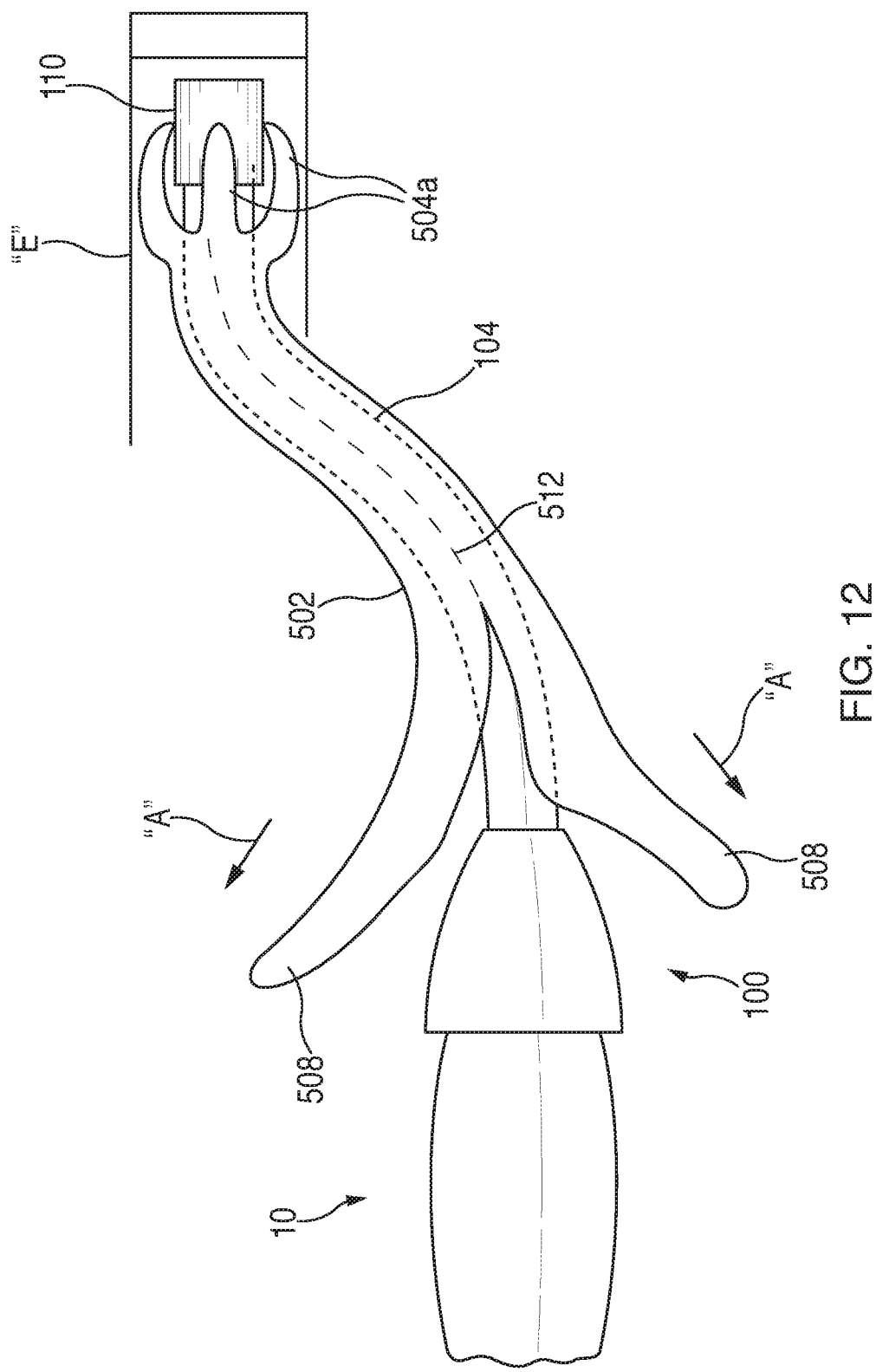
FIG. 12 is a perspective side view of the protective assembly shown in FIG. 10 received about the adapter assembly shown in FIG. 1 and received within a stump of an esophagus.

With reference now to FIGS. 10-12, another embodiment of an assembly for protecting the elongate body 104 of the adapter assembly 100 and the loading unit 110 that is secured to the elongate body 104, and for minimizing damage to tissue of a patient during introduction of the adapter assembly 100 within the patient, is shown generally as protective assembly 500. The protective assembly 500 includes a sleeve member 502, and a cap member 504 secured to a distal end of the sleeve member 502. The sleeve member 502 is configured to be received about the elongate body 104 of adapter assembly 100. The cap member 504 is configured to be releasably received about the loading unit 110 secured to the distal end of the elongate body 104 of the adapter assembly 100.

The sleeve member 502 of the protective assembly 500 is substantially similar to sleeve member 402 of the protective assembly 400 described above, and includes an elongate flexible body 506. As shown, the cap member 504 includes a substantially conical shape and may be transparent or translucent. The cap member 504 is formed of flexible plastic or other suitable material, and is divided into multiple leaves or sections 504a. For example, and as shown, the cap member 504 includes two leaves (FIG. 11A), three leaves (FIG. 11B), four leaves (FIG. 11C), or five leaves (FIG. 11D). The leaves 504a may be connected by a frangible connection 504b, e.g., weakened plastic bridges, which are configured to break during retraction of the sleeve member 502 relative to the elongate body 104 of the adapter assembly 100. The greater number of leaves 504a, the less room the cap member 504 will occupy radially as the protective assembly 500 is removed from about the elongate body 104 of the adapter assembly 100.

The elongate flexible body 506 of the sleeve member 502 may be constructed of a more flexible material than the cap member 504. The cap member 504 may be made more rigid by increasing the wall thickness of the leaves 504a or by using a stiffer material to construct the cap member 504.

As shown in FIG. 12, removal of the protective assembly 500 from about the elongate body 104 of the adapter assembly 100 requires pulling handle members 508 proximally and radially outward relative to the elongate body 104, as indicated by arrows "A", to cause tearing of the sleeve member 502 along a tear-line 512 and to cause separation of the leaves 504a of the cap member 504. As the sleeve member 502 is separated along the tear-line 512 and the sleeve member 502 is retracted proximally relative to the elongate body 104, the leaves 504a of the cap member 504 separate to permit passage of the loading unit 110 therethrough. Once completely removed from about the elongate body 104 of the adapter assembly 100, the clinician may dispose of the protective assembly 500, and the adapter assembly 100 may be used in a traditional manner.

Figure 13:
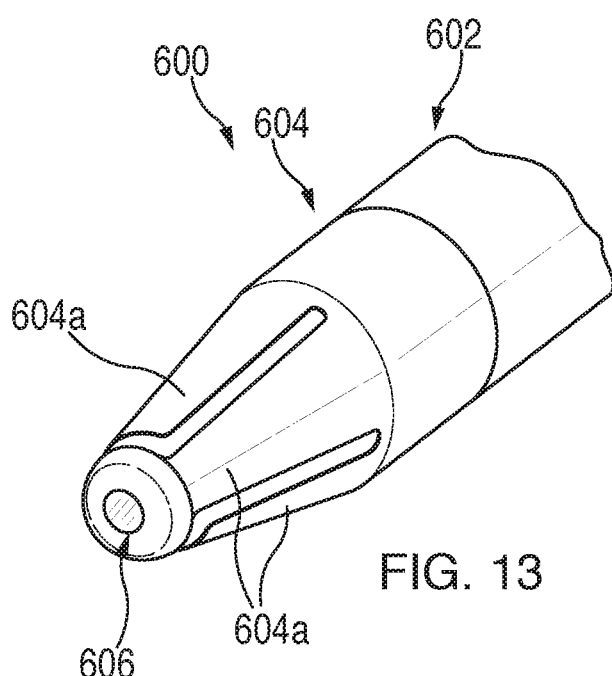
FIG. 13 is a perspective side view of the distal end of a protective assembly according to another embodiment of the present disclosure.
Figure 14:
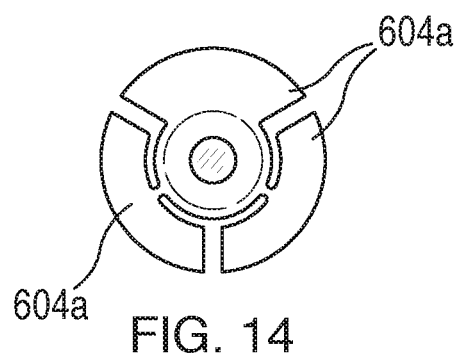
FIG. 14 is an end view of the distal end of the protective assembly shown in FIG. 13.
Figure 15:
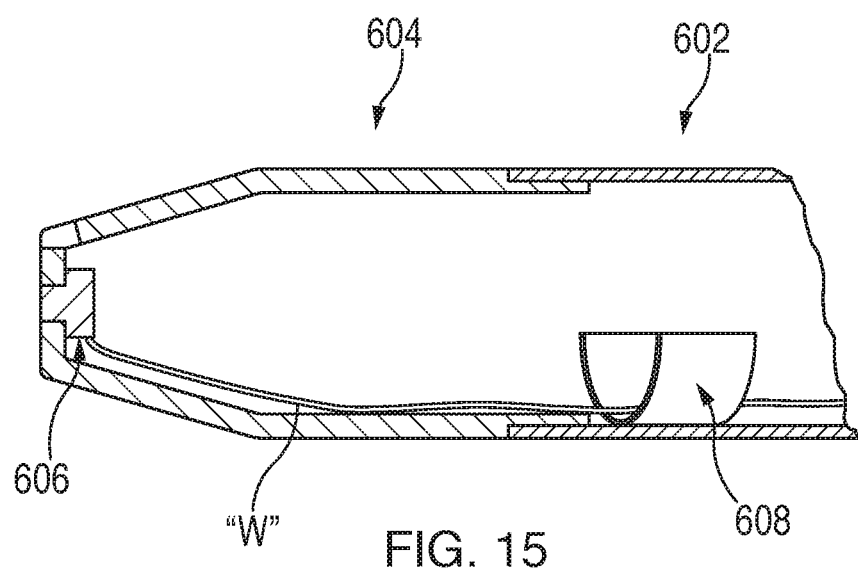
FIG. 15 is a cross-sectional side view of the protective assembly shown in FIG. 13.

Turning to FIGS. 13-15, another embodiment of an assembly for protecting the elongate body 104 of the adapter assembly 100 and an attached loading unit 110, is shown generally as protective assembly 600. The protective assembly 600 includes a sleeve member 602, and a cap member 604 secured to a distal end of the sleeve member 602. The protective assembly 600 further includes a camera assembly 606 supported within the cap member 604. The camera assembly 606 may connect with a monitoring unit (not shown) wirelessly, or through a wire "W" (FIG. 15) extending along the length of the sleeve member 602.

The cap member 604 includes a plurality of leaves 604a. The camera assembly 606 is supported on a distal end of one of the leaves 604a. The camera assembly 606 may be removable to permit reuse. The camera assembly 606 permits viewing as the elongate body 104 of the adapter assembly 100 is introduced into a patient. The camera assembly 606 may include charge-coupled device (CCD) cameras, or other suitable cameras.

Figure 16:
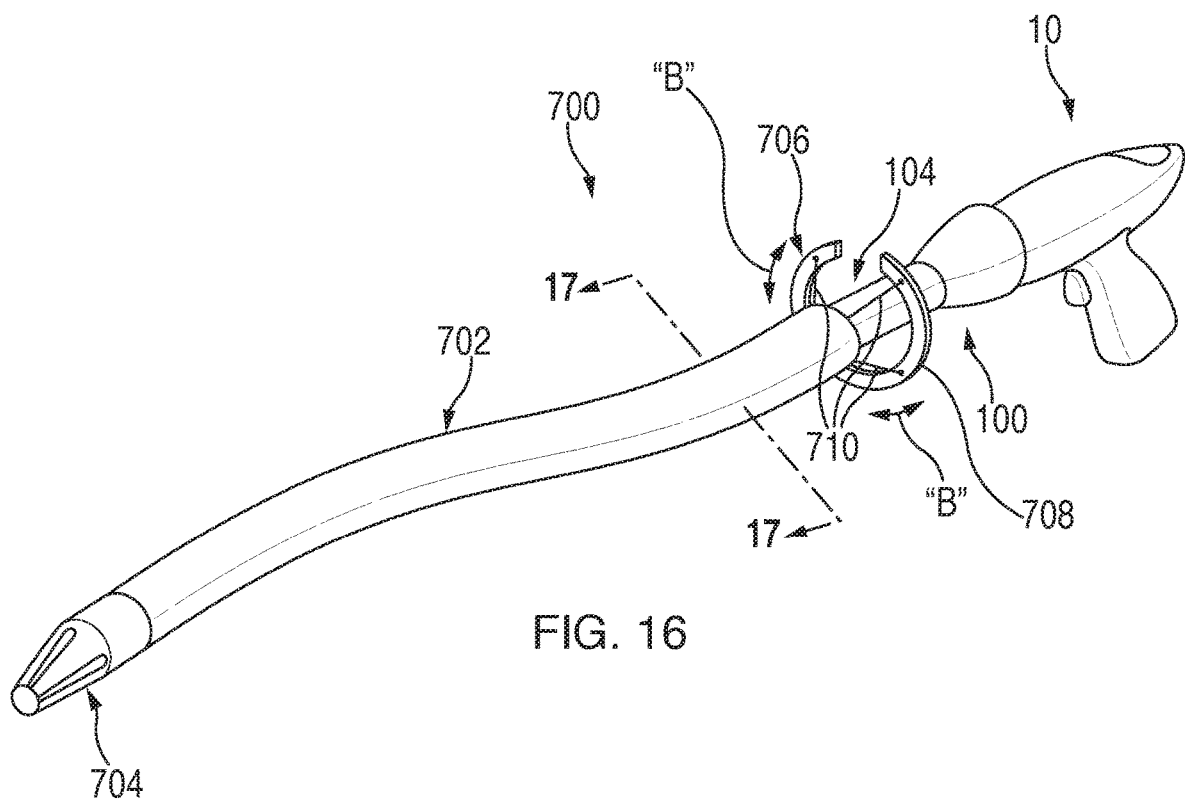
FIG. 16 is a perspective side view of a protective assembly according to another embodiment of the present disclosure received about the adapter assembly shown in FIG. 1 which is secured to the exemplary handle assembly shown in FIG. 1.
Figure 17:
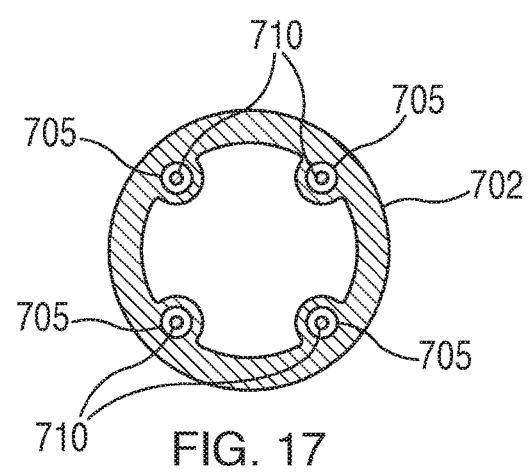
FIG. 17 is a cross-sectional end view taken along line 17-17 in FIG. 16.

With reference now to FIGS. 16 and 17, an assembly for protecting the elongate body 104 of the adapter assembly 100 and a loading unit 110 attached to the elongate body 104, is shown generally as protective assembly 700. The protective assembly 700 is substantially similar to protective assemblies 400, 500, 600 described hereinabove. The protective assembly 700 includes a sleeve member 702, a cap member 704 integrally formed with or secured to a distal end of the sleeve member 702, and a steering assembly 706 supported on and extending through the sleeve member 702.

The steering assembly 706 includes a steering ring 708, and a plurality of steering cables 710 extending from the steering ring 708 and through the sleeve member 702. The steering cables 710 are each received through a lumen 705 of the sleeve member 702. As shown, the protective assembly 700 includes four (4) steering cables 710. However, it is envisioned that the protective assembly 700 may have more or less than four (4) steering cables 710.

During a surgical procedure, after the protective assembly 700 is received about the elongate body 104 of the adapter assembly 100, the steering ring 708 may be used to guide the elongate body 104 of the adapter assembly 100 within a patient. More particularly, rotation of the steering ring 708 of the protective assembly 700 about a longitudinal axis of the adapter assembly 100, as indicated by arrows "B" in FIG. 16, causes corresponding movement of the sleeve member 702 of the protective assembly 700 which moves the elongate body 104 of the adapter assembly 100. As the adapter assembly 100 is being introduced into a patient, rotation of the steering ring 708 relative to the adapter assembly 100 facilitates continued movement of the adapter assembly 100 to the desired position.

Figure 18:
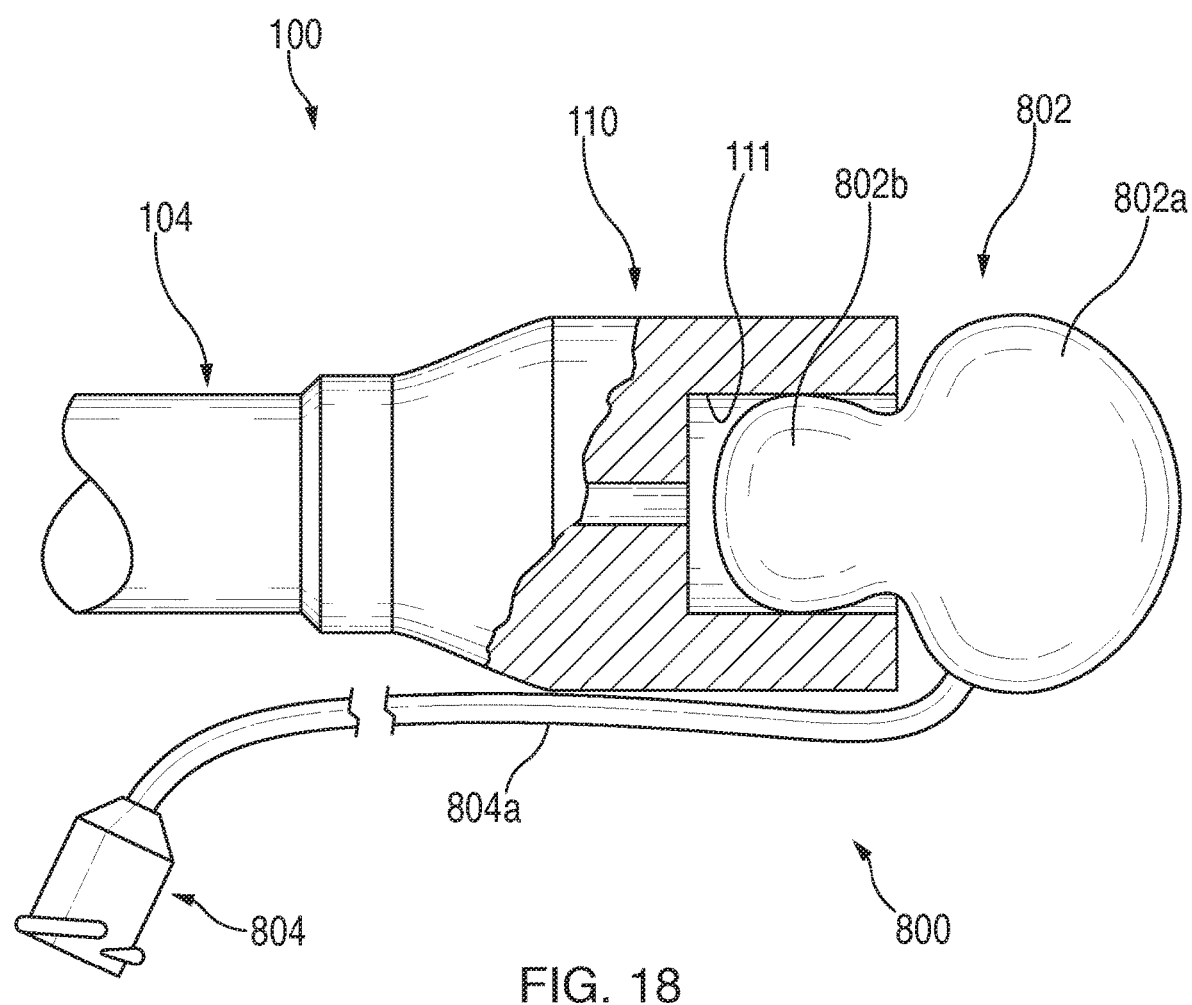
FIG. 18 is a side partial cross-sectional view of a protective assembly according to another embodiment of the present disclosure.

With reference now to FIG. 18, an assembly for protecting the loading unit 110 secured to the distal end of the elongate body 104 of the adapter assembly 100 is shown generally as protective assembly 800. The protective assembly 800 includes an inflatable member 802 configured for operable engagement of the loading unit 110, and an insufflation port 804 for effecting insufflation of the inflatable member 802. The insufflation port 804 may include a luer connector, or other suitable connection means, and is in fluid communication with the inflatable member 802 through an inflation tube 804a. The protective assembly 800 may further include a syringe, canister, bellow, or other suitable means for inflating the inflatable member 802.

The inflatable member 802 of the protective assembly has a first substantially spherical portion 802a, and a second substantially spherical portion 802b extending from the first substantially spherical portion 802a. The first substantially spherical portion 802a being greater in size or diameter than the second substantially spherical portion 802b when the inflatable member 802 is in an inflated condition. As shown in FIG. 18, when the inflatable member 802 is in the inflated condition, the second substantially spherical portion 802b is securely received within a cylindrical cavity 111 of the loading unit 110 which is secured to the distal end of the elongate body 104 of the adapter assembly 100. When the second substantially spherical portion 802b of the inflatable member 802 is received within the cylindrical cavity 111 of the loading unit 110, the first substantially spherical portion 802a covers a distal end of the loading unit 110. In this manner, the inflatable member 802 prevents contact of the distal end of the loading unit 110 with tissue as the adapter assembly 100 and the attached protective assembly 800 is introduced within a patient.

It is envisioned that the first substantially spherical portion 802a of the inflatable member 802 may be configured to match the contour of the loading unit 110. In this manner, the inflatable member 802 more closely aligns with the loading unit 110.

Figure 19:
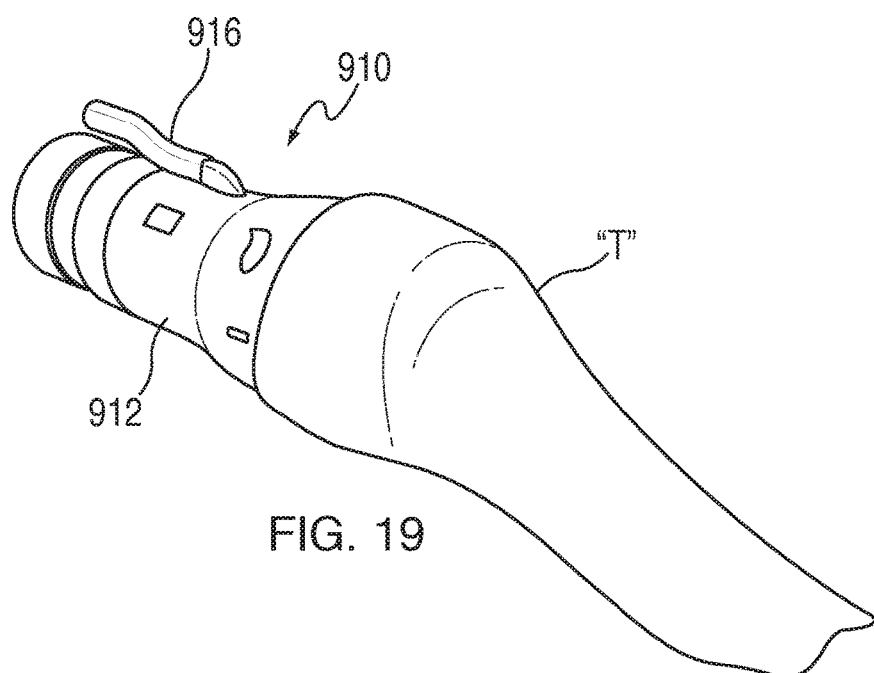
FIG. 19 is a perspective side view of a loading unit according to an embodiment of the present disclosure and a tubular organ received about a distal end of the loading unit.
Figure 20:
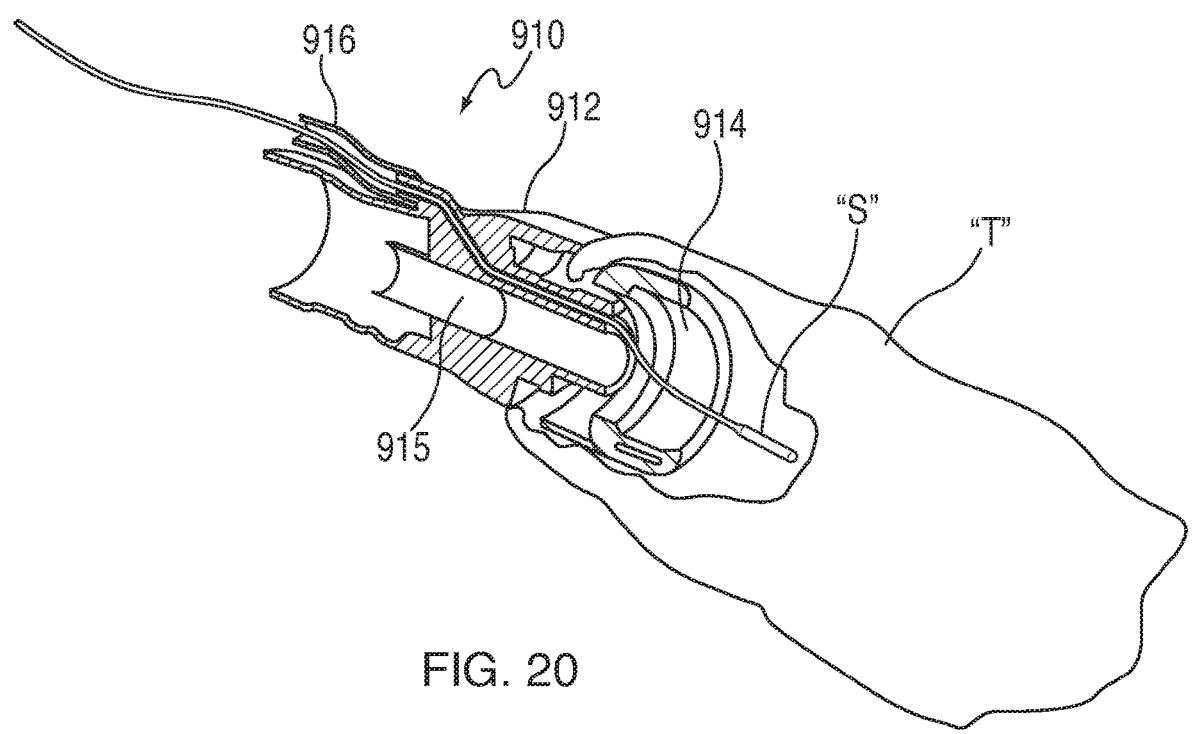
FIG. 20 is a cross-sectional perspective side view of the loading unit shown in FIG. 19.
Figure 21:
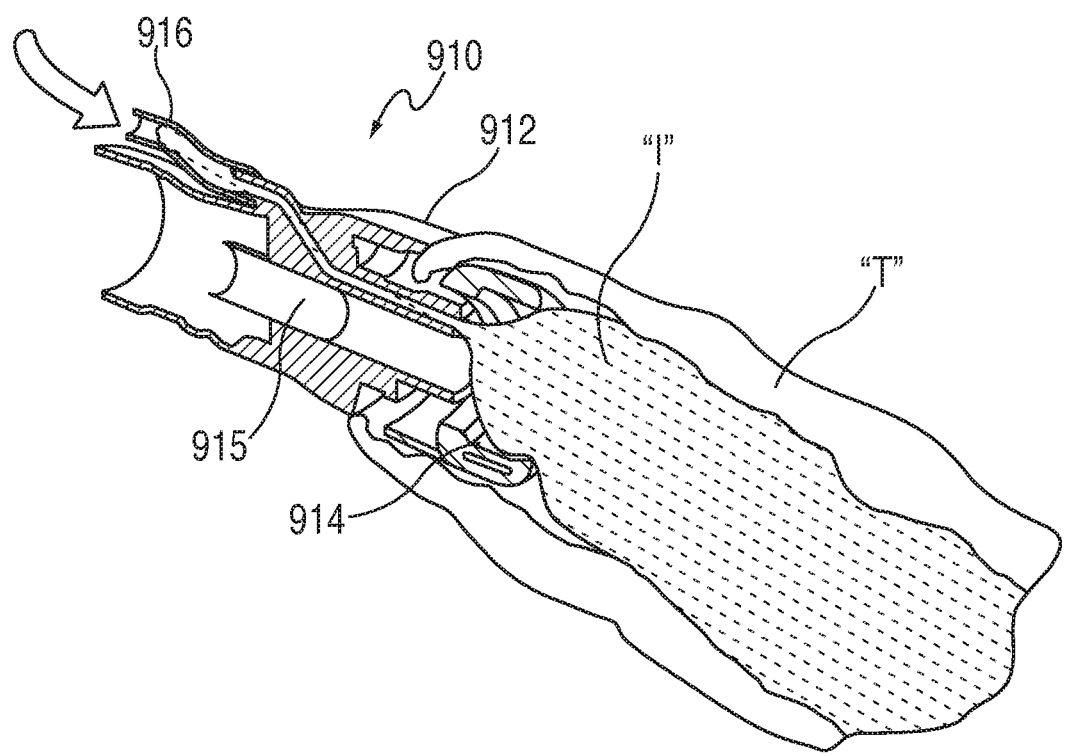
FIG. 21 is a cross-sectional perspective side view of the loading unit shown in FIG. 19 during an irrigation procedure.

With reference now to FIGS. 19-21, an embodiment of a loading unit according to the present disclosure is shown generally as loading unit 910. The loading unit 910 is configured for operable connection to the distal end of the elongate body 104 (FIG. 1) of the adapter assembly 100 (FIG. 1). Briefly, the loading unit 910 includes a shell 912 and a cartridge assembly 914 mounted on a distal end of the shell 912. The shell 912 defines a lumen 915 extending therethrough for providing a pathway through the cartridge assembly 914. The lumen 915 may be used to, for example, provide irrigation fluids "I" (FIG. 21) to the tissue being stapled "T". In addition, the lumen 915 may be used to receive, for example, guide wires, scopes "S" (FIG. 20), or other suitable instruments during a stapling procedure. A connector sleeve 916 may be received on a proximal end of the lumen 915 to facilitate receipt of a fluid and/or instrument into and through the lumen.

It is envisioned that the embodiments of the present disclosure may be modified for use with various electromechanical surgical instruments and/or electrosurgical instruments. It is further envisioned that these instruments may, for example, be configured to be detachably coupleable and controllable by a robotic surgical system.

Figure 22:
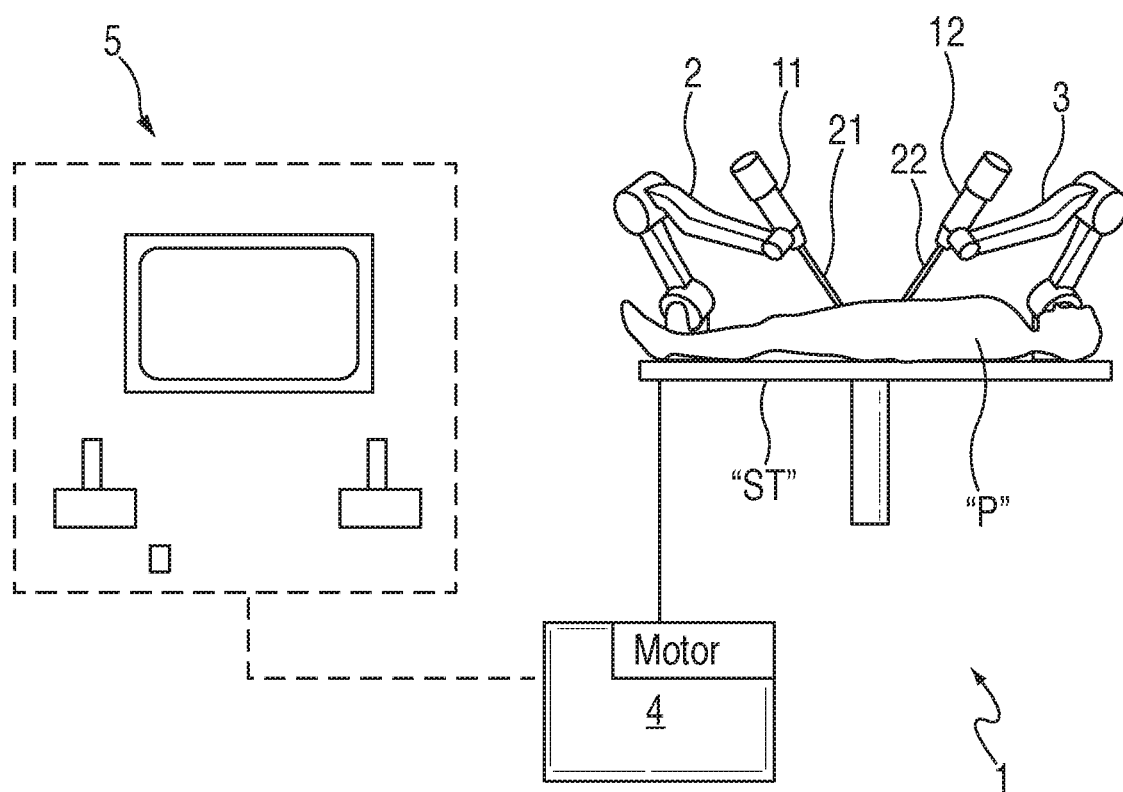
FIG. 22 is a schematic illustration of a robotic surgical system including a robotic surgical assembly suitable for use with embodiments of the present disclosure.

With reference now to FIG. 22, an exemplary robotic surgical system is shown generally as robotic surgical system 1 and, may include a plurality of surgical robotic arms, e.g., surgical robotic arms 2, 3, each having an instrument drive unit, e.g., instrument drive unit 11, 12, and an end effector, e.g., surgical stapler 21, 22, removably attached thereto; a control device, e.g., control device 5; and an operating console, e.g., operating console 4, coupled with the control device 5. As shown, the robotic surgical system 1 is configured for use on a patient "P" lying on a surgical table "ST" to be treated in a minimally invasive manner by means of the surgical stapler 21, 22.

For a detailed description of the construction and operation of an exemplary robotic surgical system, reference may be made to U.S. Patent Application Publication No. 2012/0116416, the entire contents of which are incorporated by reference herein.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for connecting a handle assembly with a loading unit, the adapter assembly comprising:
   a housing;
   an elongate body extending from the housing;
   a trocar assembly supported within the elongate body and including a trocar member, wherein the trocar member extends from the elongate body, wherein the trocar member includes a distal portion having a first polarity and a proximal portion having a second polarity; and
   an anvil assembly including a center rod releasably securable to the trocar assembly, the center rod including a proximal portion having the second polarity and a distal portion having a first polarity.

2. The adapter assembly of claim 1, wherein the anvil assembly includes a removable tip, the removable tip being magnetized to compliment the trocar member such that the removable tip is magnetically attracted to the trocar member.

3. The adapter assembly of claim 1, wherein the trocar assembly includes an electromagnet received about the trocar member for selectively magnetizing the trocar member.

4. The adapter assembly of claim 1, further including a light source.

5. The adapter assembly of claim 1, further including an electromagnet assembly, wherein the electromagnet assembly provides the trocar member with the first and second polarities.

6. The adapter assembly of claim 5, further including a power source for selectively providing power to the electromagnet assembly.

7. The adapter assembly of claim 6, further including a switch operably disposed between the power source and the electromagnet assembly for selectively providing power to the electromagnet assembly.

8. The adapter assembly of claim 5, wherein the electromagnet assembly includes a wire coil.

9. The adapter assembly of claim 5, wherein the electromagnet assembly includes a solenoid.

10. An adapter assembly for connecting a handle assembly with a loading unit, the adapter assembly comprising:
an elongate body;
a loading unit disposed on a distal end of the elongate body, the loading unit including a selectively activated electromagnet assembly; and
a trocar assembly selectively extendable relative to the loading unit and including a trocar member, wherein the trocar member is operably coupled with the electromagnet assembly such that activation of the electromagnet assembly magnetizes the trocar member.

11. The adapter assembly of claim 10, further including an anvil assembly, wherein the anvil assembly includes a center rod configured to be attracted to the trocar member when the electromagnet assembly is activated.

12. The adapter assembly of claim 10, further including a power source for selectively providing power to the electromagnet assembly.

13. The adapter assembly of claim 12, further including a switch operably disposed between the power source and the electromagnet assembly for selectively providing power to the electromagnet assembly.

14. The adapter assembly of claim 10, wherein the electromagnet assembly includes a wire coil.

15. The adapter assembly of claim 10, wherein the electromagnet assembly includes a solenoid.

\* \* \* \* \*